(12) United States Patent
Trumer et al.

(10) Patent No.: US 8,218,846 B2
(45) Date of Patent: Jul. 10, 2012

(54) AUTOMATIC PATHWAY AND WAYPOINT GENERATION AND NAVIGATION METHOD

(75) Inventors: Dror Trumer, Hadera (IL); Yaniv Nir, Tel Aviv (IL); Dorian Averbuch, Ramat HaSharon (IL)

(73) Assignee: superDimension, Ltd., Herzliya (IL)

( * ) Notice: Subject to any disclaimer, the term of this patent is extended or adjusted under 35 U.S.C. 154(b) by 388 days.

(21) Appl. No.: 12/466,238

(22) Filed: May 14, 2009

(65) Prior Publication Data
US 2010/0008555 A1    Jan. 14, 2010

Related U.S. Application Data

(60) Provisional application No. 61/053,523, filed on May 15, 2008.

(51) Int. Cl.
*G06K 9/00* (2006.01)
(52) U.S. Cl. .......................................... 382/131
(58) Field of Classification Search .................. None
See application file for complete search history.

(56) References Cited

U.S. PATENT DOCUMENTS

| | | |
|---|---|---|
| 5,480,422 A | 1/1996 | Ben-Haim |
| 5,558,091 A | 9/1996 | Acker et al. |
| 5,729,129 A | 3/1998 | Acker |
| 5,752,513 A | 5/1998 | Acker et al. |
| 5,928,248 A | 7/1999 | Acker |
| 6,016,439 A | 1/2000 | Acker |
| 6,147,480 A | 11/2000 | Osadchy et al. |
| 6,161,032 A | 12/2000 | Acker |
| 6,188,355 B1 | 2/2001 | Gilboa |
| 6,201,387 B1 | 3/2001 | Govari |
| 6,203,493 B1 | 3/2001 | Ben-Haim |
| 6,211,666 B1 | 4/2001 | Acker |
| 6,226,543 B1 | 5/2001 | Gilboa et al. |
| 6,233,476 B1 | 5/2001 | Strommer et al. |
| 6,314,310 B1 | 11/2001 | Ben-Haim et al. |
| 6,332,089 B1 | 12/2001 | Acker et al. |
| 6,335,617 B1 | 1/2002 | Osadchy et al. |
| 6,366,799 B1 | 4/2002 | Acker et al. |
| 6,373,240 B1 | 4/2002 | Govari |
| 6,427,314 B1 | 8/2002 | Acker |
| 6,453,190 B1 | 9/2002 | Acker et al. |
| 6,484,118 B1 | 11/2002 | Govari |
| 6,558,333 B2 | 5/2003 | Gilboa et al. |
| 6,574,498 B1 | 6/2003 | Gilboa |
| 6,580,938 B1 | 6/2003 | Acker |
| 6,591,129 B1 | 7/2003 | Ben-Haim et al. |
| 6,593,884 B1 | 7/2003 | Gilboa et al. |
| 6,615,155 B2 | 9/2003 | Gilboa |
| 6,618,612 B1 | 9/2003 | Acker et al. |

(Continued)

OTHER PUBLICATIONS

United States Patent and Trademark Office, Final Office Action mailed Nov. 3, 2011 in U.S. Appl. No. 11/939,537, 22 pages.

(Continued)

*Primary Examiner* — Tu Nguyen
(74) *Attorney, Agent, or Firm* — Inskeep IP Group, Inc.

(57) ABSTRACT

A navigation system for use in a luminal network of a patient, such as the airways, that is able to analyze a three-dimensional model of the luminal network and automatically determine a pathway from an entry point to a designated target. The system further automatically assigns waypoints along the determined pathway in order to assist a physician in navigating a probe to the designated target.

23 Claims, 3 Drawing Sheets

U.S. PATENT DOCUMENTS

| | | |
|---|---|---|
| 6,650,927 B1 | 11/2003 | Keidar |
| 6,690,816 B2 | 2/2004 | Aylward et al. |
| 6,690,963 B2 | 2/2004 | Ben-Haim et al. |
| 6,702,780 B1 | 3/2004 | Gilboa et al. |
| 6,711,429 B1 | 3/2004 | Gilboa et al. |
| 6,788,967 B2 | 9/2004 | Ben-Haim et al. |
| 6,833,814 B2 | 12/2004 | Gilboa et al. |
| 6,947,788 B2 | 9/2005 | Gilboa et al. |
| 6,995,729 B2 | 2/2006 | Govari et al. |
| 6,996,430 B1 | 2/2006 | Gilboa et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,517,318 B2 | 4/2009 | Altmann et al. |
| 7,831,076 B2 | 11/2010 | Altmann et al. |
| 2001/0031919 A1 | 10/2001 | Strommer et al. |
| 2001/0034530 A1* | 10/2001 | Malackowski et al. ....... 606/130 |
| 2002/0193686 A1 | 12/2002 | Gilboa |
| 2003/0074011 A1 | 4/2003 | Gilboa et al. |
| 2003/0099390 A1 | 5/2003 | Zeng et al. |
| 2003/0216639 A1 | 11/2003 | Gilboa et al. |
| 2004/0097804 A1 | 5/2004 | Sobe |
| 2004/0138548 A1 | 7/2004 | Strommer et al. |
| 2004/0249267 A1 | 12/2004 | Gilboa |
| 2005/0033149 A1 | 2/2005 | Strommer et al. |
| 2005/0085715 A1* | 4/2005 | Dukesherer et al. .......... 600/424 |
| 2005/0107688 A1 | 5/2005 | Strommer |
| 2005/0197566 A1 | 9/2005 | Strommer et al. |
| 2006/0058647 A1 | 3/2006 | Strommer et al. |
| 2006/0064006 A1 | 3/2006 | Strommer et al. |
| 2006/0149134 A1* | 7/2006 | Soper et al. ................... 600/182 |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0265639 A1* | 11/2007 | Danek et al. .................. 606/130 |
| 2007/0287901 A1 | 12/2007 | Strommer et al. |
| 2008/0033452 A1 | 2/2008 | Vetter et al. |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139915 A1 | 6/2008 | Dolan et al. |
| 2008/0147000 A1 | 6/2008 | Seibel et al. |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0247622 A1 | 10/2008 | Aylward et al. |

OTHER PUBLICATIONS

United States Patent and Trademark Office, Office Action mailed Apr. 1, 2011 in U.S. Appl. No. 11/939,537, 21 pages.

United States Patent and Trademark Office, Office Action mailed Nov. 2, 2011 in U.S. Appl. No. 12/478,573, 11 pages.

Wipo, U.S. International Search Authority, International Search Report and Written Opinion mailed Oct. 26, 2009 in International Patent Application No. PCT/IB2009/005609, 11 pages.

Wipo, U.S. International Search Authority, International Search Report and Written Opinion mailed Sep. 24, 2009 in International Patent Application No. PCT/IL2009/000569, 7 pages.

Wipo, U.S. International Search Authority, International Search Report and Written Opinion mailed Nov. 13, 2008 in International Patent Application No. PCT/IB07/04567, 8 pages.

Schmarak, Itzhak, Gera Strommer and Uzi Eichler, U.S. Appl. No. 10/986,567, filed Nov. 10, 2004, specification and drawings as filed, 81 pages.

* cited by examiner

AUTOMATIC PATHWAY AND WAYPOINT GENERATION AND NAVIGATION METHOD

RELATED APPLICATIONS

This application claims priority to Patent Application Ser. No. 61/053,523, filed May 15, 2008, entitled Automatic Pathway And Waypoint Generation And Navigation Method, which is hereby incorporated herein by reference.

BACKGROUND OF THE INVENTION

Breakthrough technology has emerged which allows the navigation of a catheter tip through a tortuous channel, such as those found in the pulmonary system, to a predetermined target. This technology compares the real-time movement of a locatable guide (LG) against a three-dimensional digital map of the targeted area of the body (for purposes of explanation, the pulmonary airways of the lungs will be used hereinafter, though one skilled in the art will realize the present invention could be used in any body cavity or system: circulatory, digestive, pulmonary, to name a few).

Such technology is described in U.S. Pat. Nos. 6,188,355; 6,226,543; 6,558,333; 6,574,498; 6,593,884; 6,615,155; 6,702,780; 6,711,429; 6,833,814; 6,974,788; and 6,996,430, all to Gilboa or Gilboa et al.; U.S. Published Applications Pub. Nos. 2002/0193686; 2003/0074011; 2003/0216639; 2004/0249267 to either Gilboa or Gilboa et al; as well as U.S. patent application Ser. No. 11/939,537 to Averbuch et al. All of these references are incorporated herein in their entireties.

Using this technology begins with recording a plurality of images of the applicable portion of the patient, for example, the lungs. These images are often recorded using CT technology. CT images are two-dimensional slices of a portion of the patient. After taking several, parallel images, the images may be "assembled" by a computer to form a virtual three-dimensional model of the lungs.

The physician then takes this virtual model and, using the software supplied with the navigation system, plans a path to the target. Planning the path to the target involves creating a patient file and selecting and saving various waypoints along the path to the target. The physician also selects and saves various registration points used by the software to register the virtual model to the actual patient in the upcoming procedure.

Typically, there is only one path that leads to the target, unless the target is very large. In the airways and vasculature of the body, the body lumina do not split and then rejoin downstream. The branches of a tree provide a good analogy: for any given leaf on a tree, there is only one combination of branches that lead to that leaf. Hence, the step of pathway planning is a time-consuming step that would be avoided if automated.

Additionally, the present systems provide guidance to the target, but not necessarily to the waypoints along the way. Instead of focusing on the target, it would be advantageous to provide navigation guidance to each of the intermittent waypoints, thereby treating each successive waypoint as a target, then, after the waypoint is reached, changing the target to the next waypoint.

SUMMARY OF THE INVENTION

In view of the foregoing, one aspect of the present invention provides a system and method for automatically planning a pathway from an entry point in a patient to a target through a luminal network.

Another aspect of the present invention automatically generates the various waypoints between a starting point and the target.

Another aspect of the present invention provides a system and method for providing navigational cues to a target via the plurality of waypoints. The cues are provided in such a manner that the next waypoint in a path is automatically detected and treated as a destination. Navigational cues are provided to that waypoint until it is reached. The system then selects the next waypoint along the path and provides navigational cues to that waypoint. This continues until the actual target is reached.

DETAILED DESCRIPTION OF THE INVENTION

Generally, the present invention includes a system and method for constructing, selecting and presenting pathway(s) to a target location within an anatomical luminal network in a patient. The present invention is particularly, but not exclusively, suited for guiding and navigating a probe through the bronchial airways of the lungs. The present invention includes a preoperative and an operative component. The preoperative component is conducted prior to navigation and can be categorized as "Pathway Planning." The operative component is conducted during navigation and can be categorized as "Navigation."

Pathway Planning

The pathway planning phase includes three general steps, each of which is described in more detail below. The first step involves using a software graphical interface for generating and viewing a three-dimensional model of the bronchial airway tree ("BT"). The second step involves using the software graphical interface for selection of a pathway on the BT, either automatically, semi-automatically, or manually, if desired. The third step involves an automatic segmentation of the pathway(s) into a set of waypoints along the path that can be visualized on a display. It is to be understood that the airways are being used herein as an example of a branched luminal anatomical network. Hence, the term "BT" is being used in a general sense to represent any such luminal network, and not to be construed to only refer to a bronchial tree, despite that the initials "BT" may not apply to other networks.

First Step—BT Generation

Figure 1:
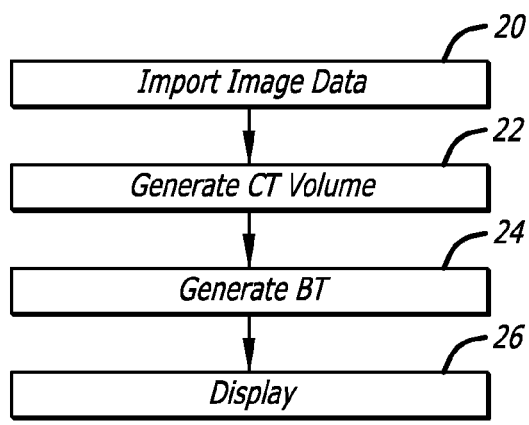
FIG. 1 is a flowchart describing a general step of a method of the present invention.

Referring now to FIG. 1, there is shown a flowchart describing the first step—using a software graphical interface for generating and viewing a BT. At 20, the first step begins with importing CT scan images, preferably in a DICOM format, into the software. The data may be imported into the software using any data transfer media, including but not limited to CDs, memory cards, network connections, etc.

At 22 the software processes the CT scans and assembles them into a three-dimensional CT volume by arranging the scans in the order they were taken and spacing them apart according to the setting on the CT when they were taken. The software may perform a data fill function to create a seamless three-dimensional model.

At 24, the software uses the newly-constructed CT volume to generate a three-dimensional map, or BT, of the airways. The three dimensional map can either be skeletonized, such that each airway is represented as a line, or it may be include airways having dimensions representative of their respective diameters. Preferably, when the BT is being generated, the airways are marked with an airflow direction (inhalation, exhalation, or separate arrows for each) for later use during the pathway generation step. It is envisioned that this step is optional. The CT volume may be used as it is.

At 26, the software displays a representation of the three-dimensional map on a user interface, such as a computer monitor.

Second Step—Pathway Selection

Figure 2:
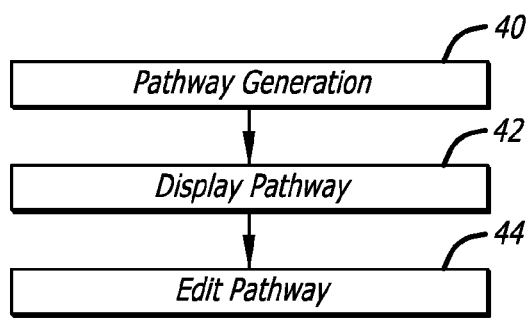
FIG. 2 is a flowchart describing a general step of a method of the present invention.

Referring now to FIG. 2, there is shown a flowchart describing the second step—using the software graphical interface for selection of a pathway on the BT. At 40, the second step begins with a determination, by the software, of an appropriate pathway to a selected target.

In one embodiment, the software includes an algorithm that does this by beginning at the selected target and following lumina back to the entry point. Using the airways as an example, the target is first selected. The software then selects a point in the airways nearest the target. If the point closest to the target is in an airway segment that is between branches, the software has to choose between two directional choices. If the airways of the BT were marked with airflow direction, the software moves in the opposite direction of the arrows, thereby automatically generating a pathway to the entry point.

Alternatively, the pathway to the target may be determined using airway diameter. Moving toward the entry point (the trachea) results in an increased airway diameter while moving distally results in a decreased airway diameter. Hence, the software could choose to move in the direction of increased airway diameter. If the point closes to the target is in an airway segment that includes one or more branches, the choices are more numerous but the following the path of the greatest increase in airway diameter will still result in the correct path to the entry point.

Though unlikely, in the event that an incorrect path is taken, the software would eventually detect an inevitable decrease in diameter, if this is the case, the software would automatically abort that path and revert to the last decision-making point. The algorithm will resume, blocking off the incorrect path as an option.

At 42, after the pathway has been determined, or concurrently with the pathway determination, the suggested pathway is displayed for user review. Preferably, the entire BT will be displayed with the suggested pathway highlighted in some fashion. The user will have zoom and pan functions for customizing the display.

At 44, the user is given the opportunity to edit and confirm the pathway. There may be reasons an alternative pathway is desirable. For example, though the targeted lesion is closest to a particular airway, there may be an artery or a lobe division between the selected airway and the target. Hence, it is important to provide the user with editing ability.

Third Step—Waypoint Selection

Figure 3:
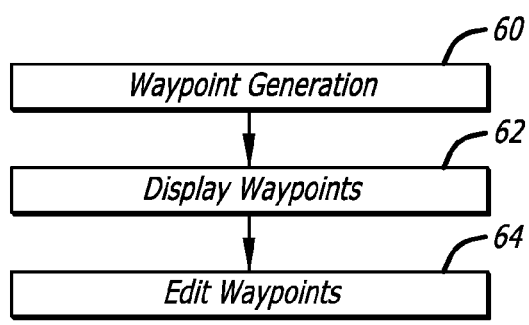
FIG. 3 is a flowchart describing a general step of a method of the present invention.

Referring now to FIG. 3, there is shown a flowchart describing the third step—using the software to automatically generate waypoints. At 60, the third step begins by designating each of the decision making points from 40 of step 2 as waypoints. This may happen concurrently with 40. Each time the software, while navigating backwards toward the trachea, was presented with navigational choices, the user navigating toward the target will necessarily also be presented with choices. Hence, it is logical to designate those decision-making points as waypoints along the path to the target.

At 62, the waypoints appear on the suggested pathway, and may be labeled in such a way as to distinguish them from each other. For example, the waypoints may be numbered, beginning at 1, in the order that they appear. Preferably, the waypoints are positioned just downstream of each bifurcation, instead of at the bifurcation. In this way, providing navigation directions to the waypoint results in the probe being positioned in the appropriate airway once the waypoint has been reached. Hence, the physician can begin navigation to the next waypoint by simply advancing the probe without being concerned about advancing down an incorrect airway.

At 64, the user is given the opportunity to edit the waypoints. It is understood that the second and third steps may occur concurrently. If the user is editing the pathway to the target, the user will also be selecting alternative waypoints, as one in the art will realize.

Fly-Through Feature

Figure 4:
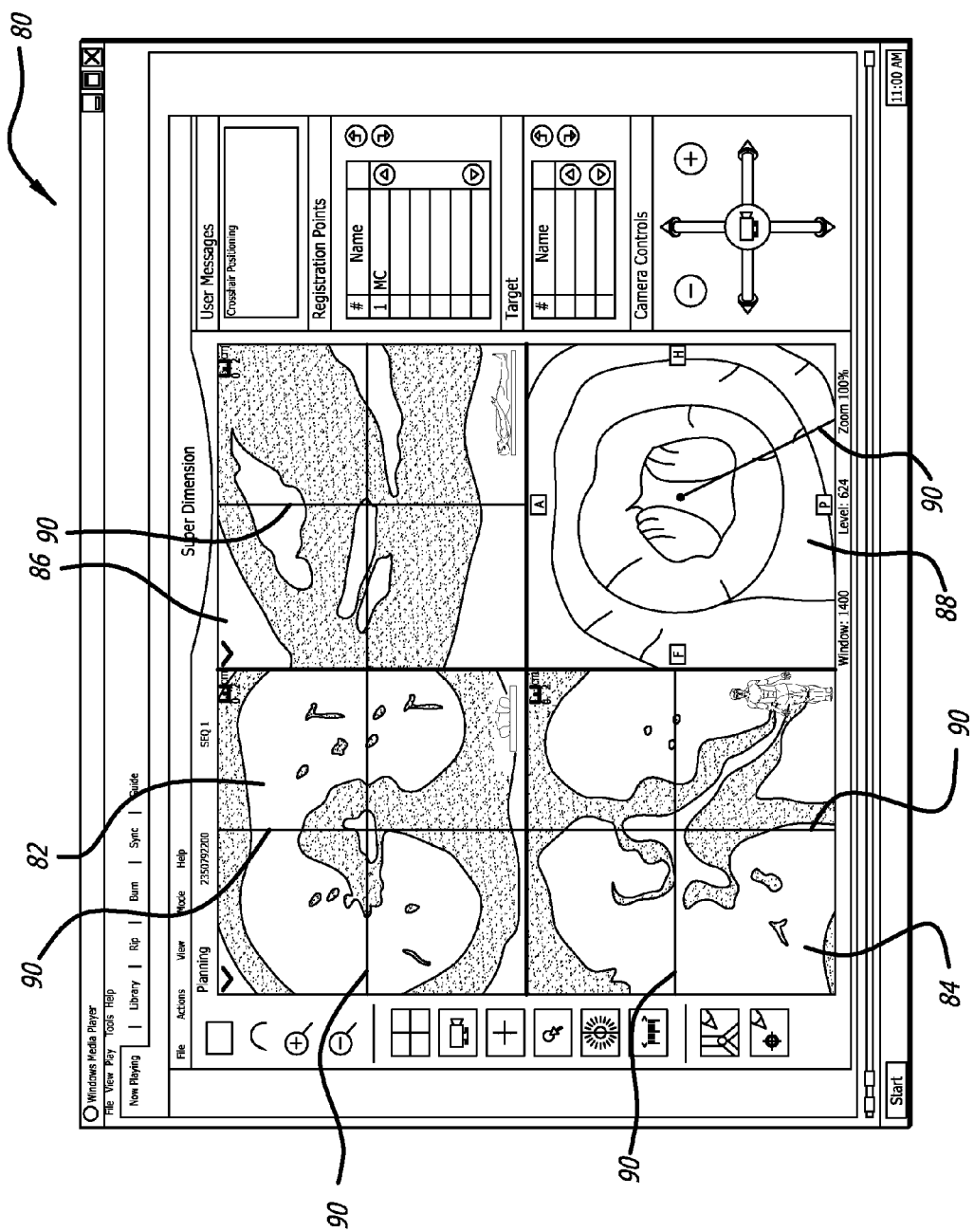
FIG. 4 is a user interface of an embodiment of the system of the present invention.

In addition to the editing features described above, the software presents a "fly-through" feature that presents the user with the opportunity to view the user interface as it would appear from start to finish if the procedure was performed as planned. A preferred embodiment of one view the user interface is shown in FIG. 4.

The interface 80 is divided into four quadrants, 82, 84, 86 and 88. The upper-left quadrant 82 is a lateral view of the CT volume of the lungs, i.e. as though looking parallel to the spine of the patient. The lower-left quadrant 84 is a birds-eye view of the CT volume of the lungs. The upper-right quadrant 86 is a side view of the CT volume of the lungs. The lower-right quadrant 88 is a three-dimensional perspective view inside a virtual airway of the BT. Cross-hairs 90 span over all of the quadrants to show the present location of the LG. The cross-hairs 90 in quadrant 88 are shown in a perspective format.

Navigation

Figure 5:
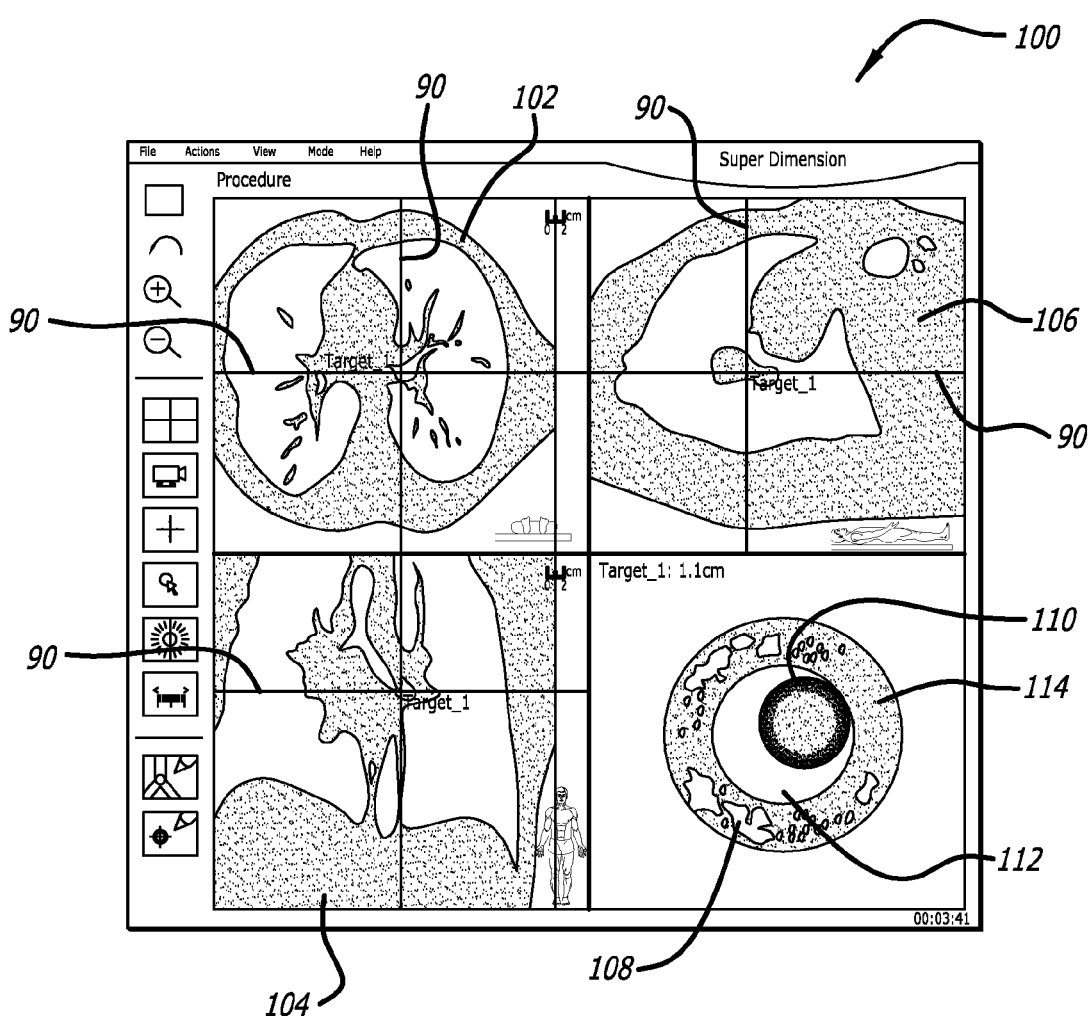
FIG. 5 is a user interface of an embodiment of the system of the present invention.

The heading "Navigation" refers to the processes occurring during the actual procedure. Referring now to FIG. 5, there is shown a user interface 100 that assists the user in navigating to the target. This view of the user interface 100 includes four quadrants 102, 104, 106, and 108. The images shown in each quadrant are preferably customizable. Hence, any of the aforementioned views from interface 80 may be displayed. However, pertinent to the navigation discussion is the view shown in the lower-right quadrant 108.

Quadrant 108 is shown as displaying an LG steering indicator. The destination 110 appears as a circle which floats over the quadrant 108 and moves when the LG is turned. The destination 110 represents the next waypoint to which the user is navigating, or the final destination (targeted lesion) in the event that the last waypoint has been passed.

When the distal tip of the LG is pointing directly at the destination 110, the destination 110 appears in the center of the circle 112. If the LG is not pointing directly at the destination 110, the destination 110 is located in a representative location in or out of the circle 112. For example, if the LG is pointing down and right of the destination 110 in the body (in other words, the destination 110 is above and left of where the LG is pointing), the destination 110 on the display in quadrant 108 will appear above and left of the center of the circle 112. If the LG is deflected away from the destination 110 far enough, the destination 110 may not even appear in the quadrant 108. For this reason, a guide arrow 114 appears some-where on the circle 112. The guide arrow 114 tells the user which direction the LG must be deflected to align the tip with the destination 110.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A method of providing a pathway through a luminal network of a patient from an entry point to a target comprising:
   collecting data regarding an anatomy of a luminal network;
   developing a three-dimensional map of said luminal network using said data;
   displaying a representation of said map on a user interface;
   selecting a target on said map;
   providing an algorithm that automatically determines a pathway from a selected entry point to said target;
   displaying said determined pathway on said user interface;
   providing an algorithm that automatically assigns and displays waypoints along said pathway.

2. The method of claim 1 wherein collecting data regarding an anatomy of a luminal network comprises taking a plurality of images of said luminal network.

3. The method of claim 2 wherein taking a plurality of images of said luminal network comprises taking a plurality of CT scans of said luminal network.

4. The method of claim 3 wherein developing a three-dimensional map of said luminal network using said data comprises assembling said plurality of CT scans and performing a data fill function to create a seamless three-dimensional model.

5. The method of claim 1 wherein developing a three-dimensional map of said luminal network comprises developing a skeletonized three-dimensional map of said luminal network.

6. The method of claim 1 wherein said algorithm automatically determines said pathway by performing steps comprising:
   beginning at said selected target;
   following lumina back to said entry point.

7. The method of claim 6 wherein following lumina back to said entry point comprises;
   selecting a point within said lumina proximate said target;
   determining a lumen diameter at said point;
   selecting a second point outside a plane of said lumen diameter;
   determining a second diameter at said second point;
   continuing to select successive points having increasing diameters until said entry point is reached.

8. The method of claim 6 wherein said luminal network comprises airways and developing a three-dimensional map of said luminal network using said data comprises labeling said map with exhalation air flow direction through said luminal network.

9. The method of claim 8 wherein following lumina back to said entry point comprises following said airflow direction labels back to said entry point.

10. The method of claim 1 wherein providing an algorithm that automatically assigns displays waypoints along said pathway comprises providing an algorithm that detects airway intersections.

11. The method of claim 10 wherein providing an algorithm that detects airway intersections further comprises providing an algorithm that detects airway intersections and designates a point spaced apart from said intersection, and on said pathway, as a waypoint.

12. The method of claim 11 wherein providing an algorithm that detects airway intersections and designates a point spaced apart from said intersection, and on said pathway, as a waypoint comprises providing an algorithm that detects airway intersections and designates a point spaced apart from said intersection toward said target, and on said pathway, as a waypoint.

13. The method of claim 1 wherein displaying said determined pathway on said user interface comprises providing a user with zoom and pan functions.

14. The method of claim 1 wherein providing an algorithm that automatically assigns and displays waypoints along said pathway comprises providing an algorithm that numbers said waypoints consecutively along said pathway.

15. The method of claim 1 further comprising providing an algorithm that generates a fly-through feature that displays a simulated navigation view from the entry point to the target on said user interface.

16. A method of providing a pathway through a luminal network of a patient from an entry point to a target comprising:
   providing a three-dimensional map of said luminal network;
   selecting a target on said map;
   providing an algorithm that automatically determines a pathway from a selected entry point to said target;
   displaying said determined pathway on said user interface.

17. The method of claim 16 further comprising providing an algorithm that automatically assigns and displays waypoints along said pathway.

18. The method of claim 17 wherein providing an algorithm that automatically assigns displays waypoints along said pathway comprises providing an algorithm that detects airway intersections.

19. The method of claim 18 wherein providing an algorithm that detects airway intersections further comprises providing an algorithm that detects airway intersections and designates a point spaced apart from said intersection, and on said pathway, as a waypoint.

20. The method of claim 19 wherein providing an algorithm that detects airway intersections and designates a point spaced apart from said intersection, and on said pathway, as a waypoint comprises providing an algorithm that detects airway intersections and designates a point spaced apart from said intersection toward said target, and on said pathway, as a waypoint.

21. The method of claim 17 wherein providing an algorithm that automatically assigns and displays waypoints along said pathway comprises providing an algorithm that numbers said waypoints consecutively along said pathway.

22. The method of claim 16 wherein displaying said determined pathway on said user interface comprises providing a user with zoom and pan functions.

23. The method of claim 16 further comprising providing an algorithm that generates a fly-through feature that displays a simulated navigation view from the entry point to the target on said user interface.

* * * * *